United States Patent
Lea

(10) Patent No.: US 9,541,478 B2
(45) Date of Patent: Jan. 10, 2017

(54) ARRAY FLUORESCENCE EQUALIZATION METHOD

(75) Inventor: Peter Lea, Toronto (CA)

(73) Assignee: SQI DIAGNOSTICS SYSTEMS INC., Toronto (CA)

( * ) Notice: Subject to any disclaimer, the term of this patent is extended or adjusted under 35 U.S.C. 154(b) by 1503 days.

(21) Appl. No.: 13/120,553

(22) PCT Filed: Oct. 7, 2009

(86) PCT No.: PCT/CA2009/001422
§ 371 (c)(1),
(2), (4) Date: Apr. 12, 2011

(87) PCT Pub. No.: WO2010/040217
PCT Pub. Date: Apr. 15, 2010

(65) Prior Publication Data
US 2011/0201522 A1   Aug. 18, 2011

(30) Foreign Application Priority Data
Oct. 8, 2008   (CA) .................................... 2640787

(51) Int. Cl.
*G01N 21/64*   (2006.01)
*G01N 1/34*   (2006.01)
*G01N 33/543*   (2006.01)

(52) U.S. Cl.
CPC ............. *G01N 1/34* (2013.01); *G01N 21/64* (2013.01); *G01N 33/54366* (2013.01)

(58) Field of Classification Search
CPC ..... G01N 1/34; G01N 21/64; G01N 33/54366
See application file for complete search history.

(56) References Cited

U.S. PATENT DOCUMENTS 6,440,645 B1 *   8/2002   Yon-Hin et al. ............... 430/322
6,550,349 B1 *   4/2003   Godin ................... B01L 3/0279
73/864.13

(Continued)

FOREIGN PATENT DOCUMENTS

JP   S54001198   6/1977
JP   1988003264   6/1986

(Continued)

OTHER PUBLICATIONS

Nielson et al. (Journal of Immunological Methods, 2004, 290:107-120).*

(Continued)

*Primary Examiner* — Jeremy C Flinders
(74) *Attorney, Agent, or Firm* — Dorsey & Whitney LLP

(57) ABSTRACT

The present invention provides a method for fluorescence intensity equalization. The method involves providing an assay device having at least one immobilized array of molecular probes that bind to an analyte bound to a fluorescent marker; providing drying apparatus comprising an aspiration tube having open first and second ends, the second end of the aspiration tube being connected a vacuum source for applying a vacuum through said tube; placing the first end of the aspiration tube in proximity of said at least one immobilized array of molecular probes; and applying a vacuum through said aspiration tube for removing vapor from said at least one immobilized array of molecular probes. The application of the present invention provides for more reliable fluorescent signal intensity readings due to a reduction in signal quenching factors.

18 Claims, 4 Drawing Sheets

(56) References Cited

U.S. PATENT DOCUMENTS

| | | |
|---|---|---|
| 6,690,461 B1 | 2/2004 | Tamura et al. |
| 2004/0203138 A1 | 10/2004 | Caren et al. |
| 2004/0241668 A1 | 12/2004 | Amorese et al. |
| 2006/0063197 A1 | 3/2006 | Anderson et al. |
| 2006/0127946 A1 | 6/2006 | Montagu et al. |
| 2008/0288179 A1 | 11/2008 | Kao et al. |

FOREIGN PATENT DOCUMENTS

| | | |
|---|---|---|
| JP | 1988269060 | 4/1987 |
| JP | H07083939 | 9/1993 |
| JP | H09311097 | 12/1997 |
| JP | 2001021558 | 1/2001 |
| JP | 2004294081 | 10/2004 |
| JP | 2008512645 | 4/2008 |
| JP | 2012504224 | 2/2012 |
| WO | WO0100324 | 1/2001 |
| WO | WO2006007766 | 1/2006 |
| WO | WO2006/031311 | 3/2006 |
| WO | WO2006058031 | 6/2006 |
| WO | WO 2010/034126 | 4/2010 |

OTHER PUBLICATIONS

Angenendt et al. (Journal of Chromatography A, 2003, 1009:97-104).*
Pena, et al., "Automated microarray drying using dual tubing," Sep. 13, 2007.
Extended European Search Report from European Application No. 09818715.6 dated Aug. 8, 2012.
International Preliminary Report on Patentability—IPRP—PCT/CA2009/001422 (6pages).
Wu, P.—"Diagnostic devices as biomaterials: a review of nucleic acid and protein microarray surface performance issues." J. Biomater. Sci. Polymer Edn. vol. 19, No. 6, pp. 725-753 (2008).
International Search Report from International Application No. PCT/CA2009/001422 dated Jan. 5, 2010.

* cited by examiner

ARRAY FLUORESCENCE EQUALIZATION METHOD

CROSS-REFERENCE TO RELATED APPLICATIONS

This application is a U.S. Nationalization of PCT International Application No. PCT/CA2009/001422, filed 7 Oct. 2009, which claims priority to Canadian Patent Application No. 2640787, filed 8 Oct. 2008. Both of the foregoing applications are incorporated herein, in their entireties, by reference.

FIELD OF THE INVENTION

The invention relates to a method of assay spot and array fluorescence intensity equalization by inducing uniform removal of fluid vapor during controlled drying of assay spot array components.

DESCRIPTION OF THE RELATED ART

An advantage of fluorescence spectroscopy is measurement and analysis of various features that are related to fluorescence quantum yield and/or lifetime of a fluorescence emitting body. The emitted fluorescence intensity is a function of emitter concentration, extinction co-efficient (absorbing power) at the excitation wavelength and quantum yield at the emission wavelength. However, time-resolved and steady-state fluorescence quenching is responsible for significant variation in fluorescence intensity measurement. Variations and heterogeneity in intensity fluctuates proportionately with fluorescence quencher concentrations, caused in part by transient effects in diffusion and the nature of the fluorophore-quencher interaction. Analysis of time-resolved frequency-domain and steady-state data has shown that quenching rates depend exponentially on the fluorophore-quencher distance from the emitter, reflecting electron transfer and exchange interactions as the probable quenching mechanisms.

Technologies for improving quantitative fluorescence signal detection emitted from assay spots and micro-arrays have been incorporated into methods for improving detection by improving detection hardware and modification of fluorescence signal processing; illustrated for example in U.S. Pat. No. 6,690,461, 2004, by Tamura et al., entitled "Methods for displaying micro-array information" which uses computer image data processing of accumulated intensities; U.S. Patent Application 200420138, 2004, by Caren et al., entitled "Polynucleotide array fabrication" which examines dried spots to illustrate resulting manufacturing errors caused by drying; U.S. Patent Application 2006/0063197 A1, by Anderson et al., entitled "Quality control and normalization methods for protein micro-arrays" which compares chemiluminescent responses by comparing buffer and printed spots for volume/concentration dye based correction; U.S. Patent Application 2006127946, by Montagu and Webb, entitled "Reading of fluorescent arrays" which compares intensity calibration features in the array itself and WO Patent Application 2006058031, by Mohammed and Dzidic, entitled "Microarray quality control" where printed spots are imaged by measuring fluorescence across spotted sample in two dimensions and then compared to printed reference images.

State of the art for deriving quantitative fluorescence measurement has emphasized on optimizing accurate detection of the signal and correction of the signal preceding signal analysis, based on the assumption that this signal correctly reflects the emitter's concentration. This approach is illustrated by European application EP 1774292, (2007) by Ge et al, entitled "A calibration slide for fluorescence detection instruments and process of preparation", which invention relates to routine calibration slides for fluorescence detection instruments, including the calibration of micro-array scanners, fluorescent microscopy, fluorescence spectrometry and fluorescence multi-well plate reading.

Current technologies for improving the coefficient of variance (% c.v.) in fluorescence intensity quantitation observed between spots and micro-arrays have been primarily focused on improving signal intensity readings obtained by modification of fluorescence signal and image processing. A method is needed for improving and setting quantitative uniformity comparison of fluorescence signal intensity between spots having identical content, when printed from a common source fluid, and to provide uniform signal levels at similar content concentrations.

There is a need for a method for inducing a uniform state of hydration by controlled drying of micro-arrays and spots to minimize fluorescence signal quenching effects of fluids and spatial distribution of spot contents e.g. particles, followed by controlled and contained removal of signal quenching fluid vapors from within and in the vicinity of the moist array and spots to enable comparative quantitative signal analysis. It is desirable to provide such method of fluid removal followed by vapor removal using a novel, simple to implement method.

There is a further need to provide for assay spot signal equalization that reduces quenching components to a relative concentration enabling enhanced comparative analysis of bio-array data using short drying time.

There is a need for such a method that randomizes any non-uniformity in the source fluorescence volume, resulting in quantitation of a more uniform illumination signal for assay spots.

There is a further need for such a method where respective divergent and diffusing quenching sources are minimized, providing comparable fluorescence signal intensities proximate to each assay spot, as measured and confirmed using a recognized reference standard to calculate a coefficient of variance (cv).

SUMMARY OF THE INVENTION

The present invention is a method for fluorescence intensity equalization; preferably by reducing quenching components to a relative concentration enabling enhanced comparative analysis of assay data. The method involves drying an assay device to remove vapor in the proximity of at least one immobilized array of molecular probes that bind to an analyte bound to a fluorescent marker.

According to an aspect of the present invention, there is provided a method for fluorescence intensity equalization comprising the following steps: providing an assay device having at least one immobilized array of molecular probes that bind to an analyte bound to a fluorescent marker; providing drying apparatus comprising an aspiration tube having open first and second ends, the second end of the aspiration tube being connected a vacuum source for applying a vacuum through said tube; placing the first end of the aspiration tube in proximity of said at least one immobilized array of molecular probes; and applying a vacuum through said aspiration tube for removing vapor from said at least one immobilized array of molecular probes.

BRIEF DESCRIPTION OF THE DRAWINGS

The present invention together with the above and other objectives and advantages may best be understood from the following detailed description of preferred embodiments of the invention illustrated in the figures, wherein.

DETAILED DESCRIPTION OF THE PREFERRED EMBODIMENTS

Figure 1:
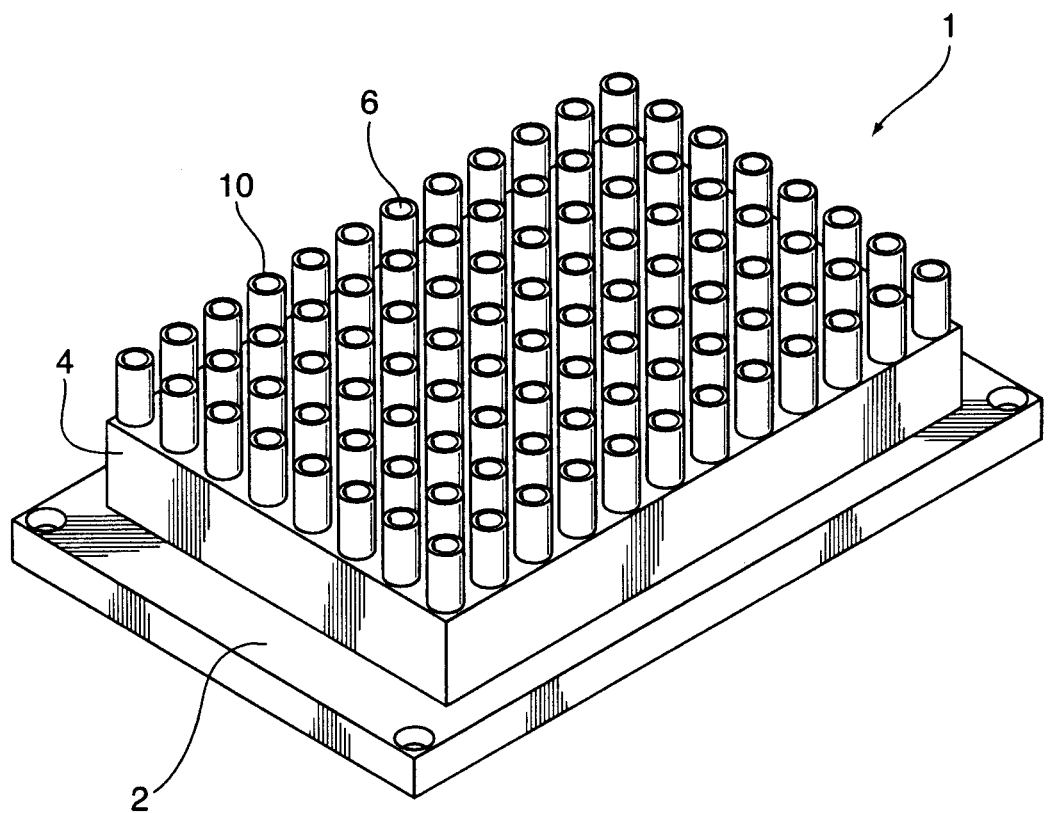
FIG. 1 is a perspective view of a preferred embodiment of a drying apparatus of the present invention.
Figure 2:
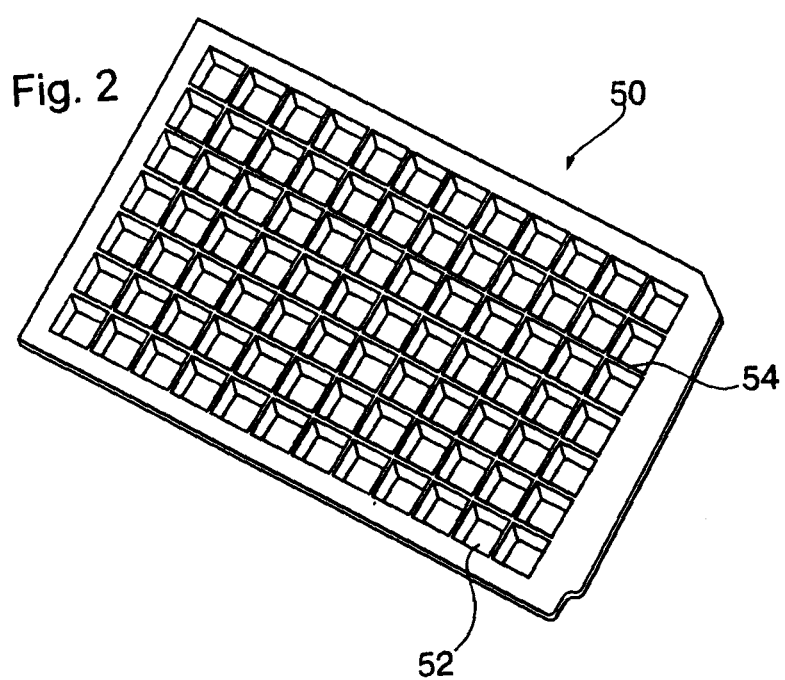
FIG. 2 is a top elevation view of an assay device used in association with the present invention.

As shown in FIG. 1, drying apparatus 1 has a frame 2. The frame 2 is can be coupled to an actuator (not shown) that moves the frame in thee dimensions along an XYZ plane. The actuator functions as a displacement means and can be one of many actuators known in the art. A preferred actuator is ELx405 Microplate Washer, BioTek Instruments, U.S.A.

Figure 3:
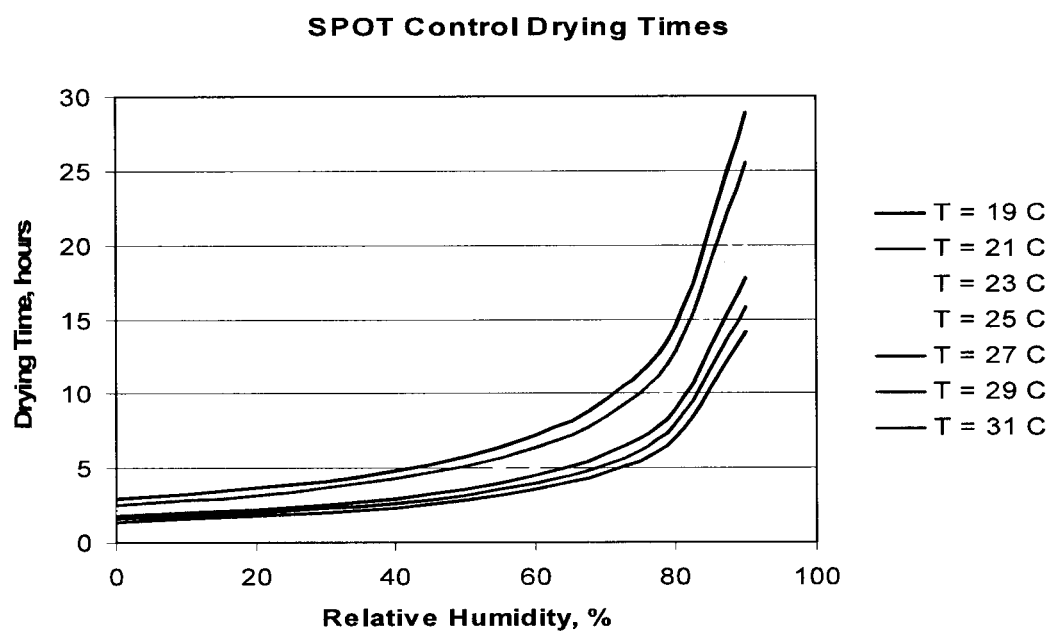
FIG. 3 is a plot of drying time versus relative humidity where drying is carried out at different temperatures.

The drying apparatus includes a housing 4 that is attached to the frame 2. A plurality of aspiration tubes 10 is located in the housing. In alternate embodiments, the dryer can have as few as one tube. Each of the tubes 10 defines a length, and defines a longitudinal bore 12 along the length between a first open end 6 and a second open end 8. As shown in FIG. 3, the longitudinal bore 12 is preferably tapered wherein the first open end 6 is has a greater diameter than the diameter of the second open end 8.

The length of the aspiration tube 10 may vary. In the preferred embodiment, the length is sufficient to maintain an aspect ratio of about 18 derived in concert with opening diameters aspect ratio of about 1.7 based on cone angle pitch at 3.5 degrees. The wall thickness of the aspiration tube 10 at the first open end 6 in proximity of a substrate is preferably about 400 µm. The diameter of the first open end 6 is about 5 mm. The second open end 6 has a diameter of about 2 mm, a preferred diameter to allow constant airflow through all aspiration tubes 10 into a vacuum head being modulated by setting of the flow access across the substrate surface area as defined by the perimeter and wall height ratio of an assay device containing a removable fluid load.

The drying apparatus 1 includes means for applying a vacuum to the second open end 8 of each aspiration tube. The means for applying a vacuum can be any of various such means known in the art. In the preferred embodiment, the vacuum means is Vacuum pump, ME 4C NT Vario, VacuuBrand, U.S.A.

Figure 4:
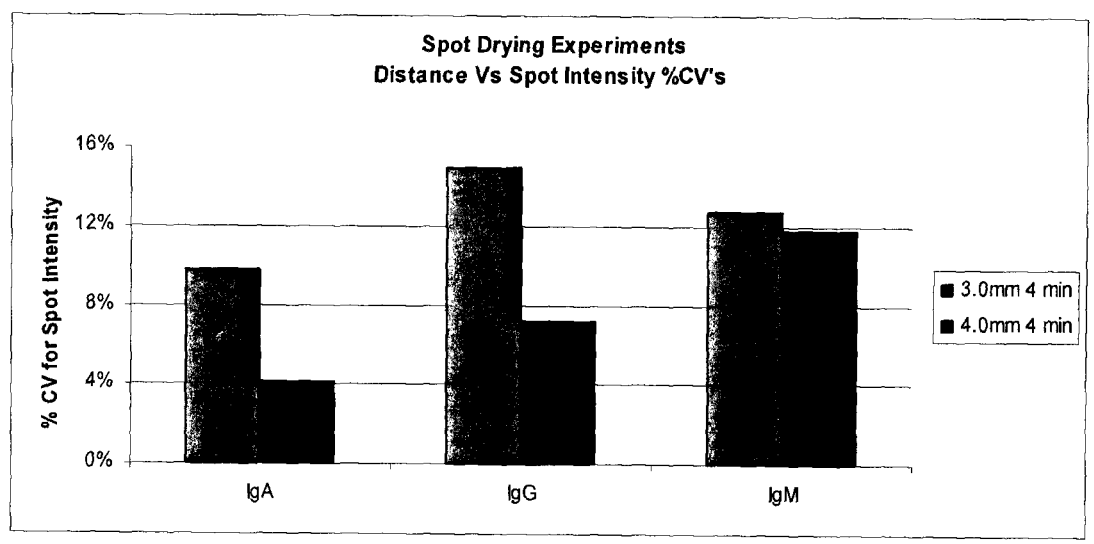
FIG. 4 is a bar graph illustrating a co-efficient of variation (% cv) for spot for immunoglobulin spots of IgA, IgG, and IgM at 4 minutes when continuous vacuum induced air flow is modulated to shear over the elevation of a spot at a distance of 3.0 mm and a distance of 4 mm.

The dryer apparatus 1 of the preferred embodiment is preferably used to dry an assay device and in particular of the type such as assay device 50 shown in FIG. 4. The assay device 50 has a plurality of wells 52. Each of said wells 50 are separated by intersecting walls 54; providing effectively a superstructure onto the plate, thereby forming a single well or separate multiple wells. Multiple wells have the added benefit of allowing multiple objects to be processed on the same plate as each well can have an assay printed thereon in form of protein spots in micro-array format, for example.

Analysis of data from bio-arrays printed on an assay device is based on the detection of fluorescence signals from labeled target molecules that specifically interact with an immobilized array of molecular probes. In the preferred embodiment, the array of molecular probes is immobilized capture antibodies printed in protein spots on the assay device. The capture antibodies bind to an antigen that is bound to a fluorescent marker. The molecular probes may be attached directly onto a substrate. In the preferred embodiment, a three-dimensional bio-array (the arrayed probes) are attached to a glass substrate by an epoxy coated substrate carrier.

In a typical protein spot assay, a fluid sample is mixed with a reagent, such as a fluorescent labelled antibody, specific to a particular analyte (the substance being tested for), such as an antigen. Another type of antibody is immobilized on a solid support in a protein spot. The fluorescent labelled antibody is mixed with the sample. A complex between the fluorescent labelled antibody, the substance being tested for and the second antibody is formed, immobilizing the marker in the protein spot. The fluorescent marker is then detected. The amount of antigen present is proportional to the intensity of fluorescence emitted from the protein spot. The preferred embodiment of the present invention is carried out on an assay device that has a plurality or array of different protein spots.

The present invention provides a method of equalizing the level of fluorescence signal emanating from assay spots wherein the capture of an analyte, labeled with a fluorescent marker, in the spots indicates the presence of the analyte. Factors that quench the level of fluorescence to be measured or otherwise distort the fluorescent signal to be measured, adversely affects the results of the assay.

In operation, the present invention provides a method for removal of vapors, especially from micro-array protein spot assay devices. In the preferred embodiment, the method is implemented by the dryer apparatus 1, and involves removing fluid vapors from the surface of an assay device typically used in washing and processing protein spot micro-arrays to effectively induce uniform states of hydration in the three dimensional protein spots that constitute a micro-array. Without being bound by theory, we have found that the micro-array constituent state of hydration directly affects the signal intensity thereby enabling enhanced quantitative analysis of bio-array data, especially when applied to diagnostic grade micro-array signals. The method of the present invention provides drying of protein spot bio-array formats without inducing negative and disruptive effects, ensuring that there is a reduction in the fluorescent signal quenching components to a relative concentration that enables enhanced comparative analysis of assay data.

Vapor removal is activated and accomplished by modulating air flow over the vapor logged, differentially hydrated substrate platform and partially dry object. Effectively, dryer apparatus 1 modulated air flow currents under controlled conditions are actively moved across vapor sources to remove vapors, resulting in a consistent state of dehydration of objects located within the vacuum induced air flow currents. The induced air flow currents simultaneously contain, isolate and disinfect the possibly contaminated and/or infectious materials carried within the consequent moist exhaust air flow.

Vapor removal is applied by drying apparatus 1 in order to equilibrate any fluid vapor present about and within a well 52. The preferred vacuum applied to air flow modulation ranges between about 106 decaPascals to about 10132 decaPascals. The X-Y co-ordinate matrix spacing of the tubes 10, in the preferred embodiment, coincides with the X-Y co-ordinate matrix placement of the well superstructure attached to the assay device 50. As both X-Y matrices provide accurate alignment, each well 52 will have a single aspiration tube 10 inserted at the centre of each well 52, with the aspiration tube 10 first opening 6 placed at a predetermined, optimal distance above the surface of the plate substrate which preferably ranges from about 20 micrometers to 5 millimeters. The preferred setting provides optimal air flow when the height of the intake end of the aspiration tube is set about 4 mm above a protein spot micro-array. Vacuum aspiration removes any residual fluid vapor.

The method of the present invention randomizes any non-uniformity in a source fluorescence volume, resulting in quantitation of a more uniform illumination signal for assay spots. Divergent and diffusing quenching sources are minimized, providing comparable fluorescence signal intensities proximate to each assay spot, as measured and confirmed using a recognized reference standard to calculate a coefficient of variance (cv).

The preferred embodiment of the present invention is a method for comparative quantitative analysis of bio-array protein spot fluorescence signal to generate intra and inter-spot uniform drying of spots by simultaneous, equivalent reduction of washing and processing fluid vapors as well as residual moisture adhering in the vicinity of the array to be analyzed. Any non-uniformity in the hydration of fluorescent arrays translates into variations in the intensity of the fluorescence signal and thus leads to erroneous interpretation of results.

FIG. 3 illustrates a comparative plot of spot relative drying time, plotted as a function of % RH (percent Relative Humidity) and temperature in ° C. (degrees Centigrade). The T (temperature) ranges from T=19° C. which correlates to the uppermost curve, to T=31° C. which correlates to the lowermost curve. In order for the requisite spots to dry by natural evaporation, as confirmed by visual inspection, the time to reach ambient residual % RH, can range from about 2 hours up to about 30 hours.

The evaporative vapor phase flux reduces the thickness of the surface film uniformly across the surface area. In the evaporation process liquid molecules interchange rapidly between the surface area and adjacent air so that this air layer becomes saturated with vapor and this vapor diffuses away from the surface. At the surface of the spot the vapor saturates to a steady state condition with diffusivity of the vapor in air. The thermal and concentration gradients caused by evaporation can induce surface tension gradient driven flows, leading to destructive impact on spot content.

FIG. 4 illustrates drying the assay spots to acceptable uniform standards within four minutes when continuous vacuum induced air flow is modulated to shear over the elevation of a spot at a distance of 3.0 mm (millimeters). Parallel air flow at a distance of 4 mm is more efficient in reducing the fluorescence measurement co-efficient of variation (% cv) for spot intensity by resulting in a further 5-6% reduction for immunoglobulin spots of IgA and IgG, with a lesser reduction for IgM.

The composite total fluorescence signal emitted from a spot when irradiated represents a volume of illumination that includes all particles and fluid contents in the illuminated volume to impact the total output signal, including signal to noise ratio due to particle concentration and thickness of the spot.

The relatively uniform state of minimal hydration that results from the preferred embodiment of this invention, confirms the impact of hydration states on the uniformity of obtained fluorescent signal. The concentration of emitter molecules in an assay spot volume produces net signal fluorescence intensity as the ratio of the number of photons emitted to the number absorbed or quenched. Fluorescence quantum yield and lifetime are modulated by increases or decreases in energy loss, effectively serving as signal quenchers, depending on concentrations of fluorophores, extinction coefficient at excitation wavelength and quantum yields. Turbid illumination volumes, i.e. assay spots, emit fluorescence from only irradiated flurophores and from which this emitted fluorescence escapes from the spot's surface. Elastic scattering events in the spot volume are produced by random spatial variations in density, refractive index and dielectric constants of non-hydrous particulates contained in a spot. These events contribute significantly to inter and intra spot fluorescence quantitative signal intensity variations.

Spots and micro-arrays prepared by embodiment of the disclosed method result in % cv's of less than 10% within 4 minutes of drying. This novel method uses an accelerated rate of drying to significantly improve micro-array assay performance as it results in consistent, accurate quantitative fluorescence signal for signal measurement.

The method of the present invention is preferably carried out to simultaneously dry all of the assay spots in multi-array matrices in a single restriction volume or well or all the assay spots in multi-array matrices in multiplexed restriction volumes or wells.

Preferably, sufficient vapor is removed to obtain a comparative relative dryness of assay spots within about ten minutes and most preferably within about five minutes.

While the present invention has been described with reference to the details of the embodiments of the invention illustrated in the figures, these details are not intended to limit the scope of the invention as claimed in the appended claims.

What is claimed is:

1. A method for fluorescence intensity equalization comprising the following steps:
   providing an assay device having a plurality of immobilized arrays of molecular probes that bind to an analyte bound to a fluorescent marker;
   providing a drying apparatus comprising a plurality of aspiration tubes, each having open first and second ends, the second end of each aspiration tube being connected to a vacuum source for applying a vacuum through said tubes, said aspiration tubes each defining a length and defining a longitudinal bore along said length, said bore having a tapered diameter such that said first end has a larger diameter than said second end;
   placing the first end of each aspiration tube in proximity of a corresponding one of said plurality of immobilized arrays of molecular probes; and
   applying a vacuum in a range between about 106 decaPascals to about 10132 decaPascals through said aspiration tubes to generate vacuum induced air flow currents for removing vapor from said plurality of immobilized arrays of molecular probes, wherein sufficient vapor is removed to obtain a uniform relative dryness of said plurality of immobilized arrays of molecular probes within about 10 minutes.

2. The method according to claim 1 wherein the first ends of the aspiration tubes are placed from about 25 micrometers to 5 millimeters from said corresponding one of said plurality of immobilized arrays of molecular probes.

3. The method according to claim 2 wherein the first end of the aspiration tubes are placed about 3 mm from the corresponding one of said plurality of immobilized arrays of molecular probes.

4. The method according to claim 1 wherein the first end of the aspiration tubes are placed about 4 mm from the corresponding one of said plurality of immobilized array of molecular probes.

5. The method according to claim 1 wherein each of said arrays of molecular probes are located in a protein spot.

6. The method according to claim 5 wherein each array of molecular probes is located on a planar surface formed in said assay device.

7. The method according to claim 6 wherein each array of molecular probes is located in a well formed in said assay device.

8. The method according to claim 1 wherein the molecular probes are antigens bound to said assay device.

9. The method according to claim 1 wherein the molecular probes are capture antibodies bound to said assay device.

10. The method according to claim 1 wherein the molecular probes are proteins bound to said assay device.

11. The method according to claim 5 wherein the protein spots are attached to the assay device by an epoxy coated substrate carrier.

12. The method according to claim 11 wherein the assay device includes a support made of glass, the capture analytes being attached to the assay device by an epoxy coated substrate carrier.

13. The method according to claim 12 wherein the step of applying a vacuum through said aspiration tube generates induced air flow currents over said plurality of immobilized arrays of molecular probes to remove residual fluid and vapor.

14. The method according to claim 13 wherein the vacuum applied creates a continuous airflow current.

15. A method for fluorescence intensity equalization, the method comprising:
providing an assay device having a plurality of immobilized arrays of molecular probes that bind to an analyte bound to a fluorescent marker;
providing a drying apparatus comprising a plurality of aspiration tubes having open first and second ends, the second end of the aspiration tubes being connected a vacuum source for applying a vacuum through said tubes;
placing the first end of the aspiration tubes in proximity of a corresponding one of said plurality of immobilized arrays of molecular probes; and
generating a uniform relative dryness of said plurality of immobilized arrays of molecular probes within about 10 minutes thereby substantially equalizing fluorescence intensity between said plurality of immobilized arrays of molecular probes by applying a vacuum through said aspiration tubes for removing vapor from said plurality of immobilized arrays of molecular probes.

16. The method according to claim 15 wherein air flow current is induced by the vacuum applied between $10^{-3}$ Torr and 1 atmosphere of pressure.

17. The method according to claim 15 wherein sufficient vapor is removed to obtain a uniform relative dryness of said plurality of immobilized arrays of molecular probes in within about three minutes.

18. The method according to claim 17 wherein sufficient vapor is removed to obtain efficient levels of uniform dryness of said plurality of immobilized arrays of molecular probes in about one minute using pre-treated shear air flow.

* * * * *